United States Patent
Becker et al.

[11] Patent Number: 6,068,844
[45] Date of Patent: May 30, 2000

[54] INCREASED RESISTANCE TO STROKE BY DEVELOPING IMMUNOLOGIC TOLERANCE TO MYELIN OR COMPONENTS THEREOF

[75] Inventors: Kyra J. Becker, Seattle, Wash.; John M. Hallenbeck; Richard M. McCarron, both of Kensington, Md.

[73] Assignee: The United States of America as represented by the Department of Health and Human Services, Washington, D.C.

[21] Appl. No.: 08/994,293

[22] Filed: Dec. 19, 1997

[51] Int. Cl.[7] .......................... A61K 38/04; A61K 38/17; C07K 1/00
[52] U.S. Cl. .......................... 424/184.1; 424/810; 514/2; 514/12; 530/350
[58] Field of Search ................ 424/184.1, 810; 514/2, 12; 530/350

[56] References Cited

U.S. PATENT DOCUMENTS

| | | | |
|---|---|---|---|
| 5,571,500 | 11/1996 | Hafler et al. | 424/43 |
| 5,641,474 | 6/1997 | Hafler et al. | 424/43 |
| 5,643,868 | 7/1997 | Weiner et al. | 514/3 |
| 5,645,820 | 7/1997 | Hafler et al. | 424/41 |
| 5,651,993 | 7/1997 | Edelson et al. | 424/534 |

OTHER PUBLICATIONS

Becker, KJ et al. Proc. Natl. Acad. Sci. (USA) vol. 94 pp. 10873–10878, Sep., 1997.
Kitamura, K et al. Biochim. Biophys. Acta. 379:582–591, 1975.
Tisch, R and McDevitt, HO. Proc. Nat. Acad. Sci. (USA) 91:437–438, Jan. 1994.
Brostoff, S. et al. Nature. 235:210–212, Feb. 1972.
Al–Sabbagh, A. et al. in: Autoimmune Disease Models: A Guidebook. Cohen and Miller, eds. Academic Press, San Diego, pp. 15–22, 1994.
Brocke, S. et al. in: Autoimmune Disease Models: A Guidebook. Cohen and Miller, eds. Academic Press, San Diego, pp. 1–14, 1994.
Gregorian, SK. et al. Cellular Immunology. 150:298–310, Sep. 1993.
Day, MJ. et al. J. Neuroimmunol. 34(2–3):197–203, Nov. 1991.

(List continued on next page.)

*Primary Examiner*—David Saunders
*Assistant Examiner*—F. Pierre VanderVegt
*Attorney, Agent, or Firm*—Fitch, Even, Tabin & Flannery

[57] ABSTRACT

The present invention relates to a method of inducing oral tolerance to ischemic injury which has the objective of minimizing the severity and size of injured regions in the brain that arise as a result of ischemia. The method responds rapidly to the onset of infarction, with treatment that is short in duration. The procedure is specifically focused on the injured area of the infarct by virtue of being targeted immunologically to the ischemic site. The method therefore avoids the possibility of inducing systemic side effects affecting other organs of the patient. The present invention involves administering myelin or a component thereof such as myelin basic protein or proteolipid protein to a subject either orally or by inhalation. The amount administered and the duration of the treatment are effective to minimize the size and severity of the infarct in the brain of the subject. The method is intended for acute conditions related either to an actual recent cerebral ischemic event or to a potential ischemic event that might arise as a result of medical or surgical treatment planned for the subject.

21 Claims, 1 Drawing Sheet

OTHER PUBLICATIONS

Weiner et al., "Double–Blind Pilot Trial of Oral Tolerization With Myelin Antigens in Multiple Sclerosis", Science, vol. 259. Feb. 26, 1993, pp. 1321–1324.

Weiner, "Oral Tolerance For The Treatment of Autoimmune Diseases", Annu. Rev. Med. 1997, 48:341–51.

Wang et al., "Myelin antigen reactive T cells in cerebrovascular diseases", Clin. exp. Immunol. (1992) 88, 157–162.

Hohol et al., "Three–year Open Protocol Continuation Study of Oral Tolerization With Myelin Antigens in Multiple Sclerosis and Design of a Phase III Pivotal Trial", Annals New York Acad. of Science, vol. 778, 1996, pp. 243–250.

Al–Sabbagh et al., "Decreased CNS Inflammation and Absence of Clinical Exacerbation of Disease After Six Months Oral Administration of Bovine Myelin in Diseases SJL/J Mice With Chronic Relapsing Experimental Autoimmune Encephalomyelitis", Journal of Neuroscience Research 45:424–429 (1996).

Mandai et al., "Ischemic Damage And Subsequent Proliferation of Oligodendrocytes in Focal Cerebral Ischemia", Neuroscience vol. 77, No. 3, pp. 849–861, 1997.

Kelly et al., "Oral tolerance in EAE: reversal of tolerance by T helper cell cytokines", Journal of Neuroimmunology 66 (1996) 77–84.

INCREASED RESISTANCE TO STROKE BY DEVELOPING IMMUNOLOGIC TOLERANCE TO MYELIN OR COMPONENTS THEREOF

FIELD OF THE INVENTION

The present invention relates to a method of minimizing the size and severity of stroke in a mammalian subject. The method involves the development of immunologic tolerance to myelin or a component thereof, such as myelin basic protein, by means of oral administration or inhalation.

BACKGROUND OF THE INVENTION

The mammalian gut is provided with specialized tissues of the immune system that serve several related functions. A principal tissue carrying out these functions is the Peyer's patches, specialized sites facing the lumen of the gut. Peyer's patches sample the contents of the lumen, process antigen, and develop an immune response. This response can lead to either cell mediated or humoral immunity, or it can lead to immunologic tolerance. The type of immune response that develops depends upon how the antigen is processed and the current physiological milieu within the Peyer's patches. Analogous immune processes are believed to occur in the airways involved in breathing.

In a fashion analogous to the development of tolerance by the mucosal immune tissues to ingested antigen, early in life the immune system of an animal also develops tolerance to the macromolecules within its own body that could otherwise serve as potential immunogens. The immune system recognizes as "self" the constituents of the body that normally reside therein, and eliminates those of its components that, if not eliminated, would react immunologically against these potential self immunogens. In certain pathological instances, however, the immune system subsequently develops an immunologic response against a self immunogen. This may occur at any time in the life of an animal. In such an event, the components of the immune system react in an immunospecific fashion with the self immunogen, or autoimmunogen, leading to any of a variety of pathological conditions. Examples include multiple sclerosis, in which the self immunogen is myelin or a component thereof, uveitis, in which the self immunogen is the S antigen, a component of the retina; rheumatoid arthritis, in which the self immunogen is one of the classes of collagen which occur in cartilage at the locus of joints; and so on. In such cases, naturally occurring components that were once recognized as "self" become treated as "foreign."

The immunological mechanisms associated with oral tolerization may be classified as active suppression, clonal anergy, and clonal deletion. In general, depending on conditions, these mechanisms may operate independently or in combination. The distinction between these mechanisms depends primarily on the dose of antigen detected by the mucosal tissues, and by the incidence of dosing. Active suppression occurs with repetitive low doses of antigen, in which the result is induction of regulatory $T_{h2}$ and $T_{h3}$ cells. These cells, when restimulated by the autoantigen, secrete cytokines such as transforming growth factor (TGF)-beta, interleukin (IL)-4, and IL-10, which act to suppress inflammatory responses. Clonal anergy may result with high doses of antigen. A state of unresponsiveness is induced in $T_{h1}$ cells, whereby their T cell receptors become incapable of responding to the specific antigen, when processed and presented by the major histocompatibility complex on an antigen presenting cell, that would normally trigger their activation. Clonal deletion, in contrast, occurs upon a single administration of a very high dose of the autoantigen, and results in actual destruction of the T cell clones bearing the specific T cell receptor responsive to the processed antigen. In the presence of high concentrations of antigen in the gut, it is believed that T cells specific for that antigen are eliminated, both within the Peyer's patch itself as well as in the thymus gland.

In recent years a therapeutic approach to the treatment of autoimmune diseases has been the development of tolerance by means of oral administration of the autoimmunogen related to the disease (Weiner, Annu. Rev. Med. 48: 341–351 (1997)). Multiple sclerosis is thought to result from T cells that recognize myelin components of the central nervous system and incite an immune response. Major components of myelin include myelin basic protein and proteolipid protein. Weiner et al. (Science 259: 1321–1324 (1993)) report that multiple sclerosis patients who were fed daily capsules of bovine myelin had a decreased incidence of attacks, compared to patients in a control group. The number of T cells reactive to myelin basic protein were reduced in the patients that were fed myelin. The dose of bovine myelin was 300 mg given daily for a period of one year. In a followup study using some of the same patients (Hohol et al., Annals N.Y. Acad. Sci. 778: 243–250 (1996)), the same dosing regime was followed for a total of three years. In some female patients a dose of 30 mg daily was pursued for one year without any apparent benefit; these patients were subsequently restored to the 300 mg/day dose. Hohol et al. also disclose a planned two-year multi-center Phase III trial which will involve the same 300 mg/day dose of bovine myelin. Such an extended period of dosing may be necessary to discern any benefit in such a chronic disease, in which patients suffer attacks relatively infrequently.

Weiner (1997) reports several clinical trials of oral tolerance at various stages of progress for treatment of various autoimmune diseases. U.S. Pat. No. 5,643,868 to Weiner et al. discloses administration of insulin by non-parenteral routes as a means for preventing or minimizing Type I, or insulin-dependent, diabetes mellitus in a subject. Oral or enteric formulations are disclosed containing between about 1 mg to about 1000 mg insulin per dose. In non-obese diabetic mice, experimental feeding regimes were, for example, twice weekly for 4 ½ weeks, then once a week for 33 weeks. In such animals, diabetes was prevented at 1 mg doses, but not when the dose was reduced to one-tenth or one-hundredth of that amount.

U.S. Pat. No. 5,651,993 to Edelson et al. discloses pharmaceutical compositions and methods of altering the immune response of a mammal. The pharmaceutical compositions contain antigens related to the particular medical state or pathology for which the immune response was intended to be altered. Administration of such compositions stimulates the antigen presenting cells. The methods entail extracorporeal treatment of the resulting expanded population of antigen presenting cells with the antigen in order to maximize the expression of major histocompatibility complex molecules bound with the antigen-derived peptides. The goal was to immunize patients against malignant cells or lymphocytes responsible for autoimmune disease.

U.S. Pat. Nos. 5,571,500, 5,641,474, and 5,645,820 to Hafler et al. also disclose methods for preventing or treating autoimmune diseases in mammals. An autoantigen specific for the autoimmune disease to be prevented or treated is administered by means of an aerosol composition containing the autoantigen. The autoantigen may include or be replaced by autoimmune suppressive fragments of the autoantigen. Autoimmune diseases treated include multiple sclerosis, rheumatoid arthritis, and others. In experimental models using rats, dosages were delivered either orally or by aerosol over periods ranging from 10–31 days before an immunization that induced an autoimmune condition, to 4 days after the immunization.

Oral tolerance to experimental autoimmune encephalomyelitis (EAE) can be induced in rats by the feeding of myelin. EAE is an animal model of inflammatory demyelinating disease which is considered to be similar to multiple sclerosis. Chronic relapsing EAE was induced in mice by immunizing with murine spinal cord (Al-Sabbagh et al., J. Neurosci. Res. 45: 424–429 (1996)). After the onset of symptoms, groups of mice were orally administered bovine myelin in doses of 1, 10, and 20 mg, respectively, three times weekly for six months. Histological examination showed treated animals had diminished inflammatory and demyelinating foci in the brain and spinal cord after prolonged oral administration of myelin. A milder manifestation of clinical disease was observed in the mice treated with 10 or 20 mg as compared to controls.

In oral tolerance experiments on EAE conducted in animals, myelin basic protein (MBP), a major component of myelin, was fed prior to injection of MBP in order to induce the disease. On examining the antibody isotypes from different lymphoid tissues in such animals, Kelly et al. (J. Neuroimmunol. 66: 77–84 (1996)) found that anti-MBP antibodies change isotype distribution most strongly in mucosal lymphoid tissues (i. e., the Peyer's patches). There was a selective reduction in anti-MBP IgA, but not in IgM.

Immune mechanisms contribute to cerebral ischemic injury. Inflammation plays a role in propagating the damage induced by cerebral ischemia. Thus stroke victims are considered to be candidates for various interventions that modulate immune system responses. Immunosuppressive agents that minimize inflammatory responses improve the outcome in experimental models of stroke. Most available immunosuppressive agents, however, have detrimental systemic side effects that limit their therapeutic use in stroke.

Molecular and cellular mechanisms underlying ischemia in the brain were investigated by Mandai et al. (Neurosci. 77 (3): 849–861 (1997)). In situ hybridization for the mRNA encoding proteolipid protein (PLP), a major component of myelin, showed attenuation of the mRNA 12 hours after middle coronary artery occlusion, and barely detectable amounts of the mRNA at 24 hours. In the ischemic core, immunohistochemistry showed that microtubule associated protein 2 disappeared, and that extensive extravasation of albumin across the blood-brain barrier had occurred. These results show extensive damage to oligodendrocytes after ischemic neuronal damage, and significant breakdown of the blood-brain barrier. In contrast, myelin basic protein was detected as long as five days after ischemia.

An immunogenic response in acute ischemic cerebrovascular diseases has been found to involve expansion of the population of T cells reactive with myelin basic protein, peptides fragments of myelin basic protein, and proteolipid protein (Wang et al., Clin. Exp. Immunol. 88: 157–162 (1992)). The T cell group studied was that which secreted interferon-gamma. Patients suffering acute ischemic cerebral infarction had a far higher number of such T cells than did patients with inflammatory neurological diseases such as aseptic meningitis, aseptic encephalitis, or other neurological diseases. In evaluating these results in relation to analogous studies on multiple sclerosis patients, Wang et al. found the origin and role of the immune responses leading to the presence of autoreactive T cells specific for MBP, MBP peptides and PLP to be unclear.

From the above summary, therefore, it is seen that treatments for stroke and related acute cerebral ischemic injury that specifically diminish the immunological response to the ischemic injury, especially ones that reduce the inflammatory response, are not available. This response involves, in particular, neutrophils, T-cells, and natural killer cells. Methods of treating cerebral ischemic injury that specifically target the infarcted area but do not significantly affect other organs in the patient are also not available. The methods currently available have significant systemic side effects when given to a patient.

Other origins of cerebral infarction are also known. Hemorrhagic stroke, and trauma that produces contusion, for example, lead to extended or focal hematomas which can result in inflammatory responses such as edema. Immune-mediated injury likewise can arise following infections such as herpes simplex encephalitis and cytomegalovirus infection.

In the treatment of cerebral ischemic injury (e.g., stroke), and of infarction originating from other causes, there remains a need for methods to minimize or eliminate the immunologic response to substances in the brain that are normally sequestered from the immune system. Breakdown of the blood-brain barrier, to the extent that it occurs, allows exposure of such substances to the immune cells in the circulatory system and facilitates an autoimmune response, including inflammation, to brain tissue, which is absent under normal circumstances. Thus, there remains a need to reduce the severity and extent of such an inflammatory response. There also remains a need for a method of treatment that specifically targets the region of the ischemic injury. Furthermore, there is a need for a method of treatment which does not carry with it the potential for systemic side effects. The present invention satisfies these needs.

SUMMARY OF THE INVENTION

The present invention provides a method of inducing oral tolerance to ischemic and hemorrhagic injury which minimizes the severity and size of injured regions in the brain that arise as a result of the injury. Such conditions develop as a result of acute medical conditions, so that the method necessarily responds rapidly to the onset of these conditions, with treatment that is short in duration. The method is specifically directed to the area injured by the infarct, by virtue of being targeted immunologically to the ischemic site. The method therefore also reduces the risk of systemic side effects affecting other organs of the patient.

The method of the invention relates to treating a mammalian subject at risk of developing injury due to an infarct in the brain. It is anticipated that as a result of such treatment the size and severity of any infarct that develops is minimized. An important step of the method entails administering myelin, or a component of myelin such as myelin basic protein or proteolipid protein, to a subject either orally or by inhalation. The amount administered and the duration of the treatment are effective to minimize the size and severity of the infarct in the brain of the subject. The method is intended for a subject at risk of infarct that is associated with, or results from, an acute medical condition. Such a condition is either a recent cerebral ischemic event or a potential ischemic event that might arise as a result of medical or surgical treatment planned for the subject. Additionally the method is directed toward subjects at risk for developing cerebral infarct associated with, or resulting from, a chronic medical condition. Such a condition may be either a genetic predisposition to stroke or a medical condition that is understood to increase the probability of incurring a cerebral infarct. The latter medical conditions include, by way of nonlimiting examples, atherosclerosis, previous stroke or transient ischemic attacks, diabetes mellitus, hypertension, hypercholesterolemia, and a history of smoking. Diagnostic and/or pathological characterization of stroke victims has identified numerous additional medical conditions producing stroke that are widely known to practitioners of internal and neurological medicine. Thus this method can be used for patients who have suffered a stroke as well as patients who are at significantly increased risk of a stroke.

DETAILED DESCRIPTION OF THE INVENTION

As used herein, the term "tolerance" or "tolerization" relates to the phenomenon or the method of developing immunological tolerance to an autoantigen by oral feeding or inhalation. Oral tolerance is developed by oral adminis tration of a composition containing the autoantigen or a closely related substance. In addition, tolerization may also be achieved by administration via inhalation. For purposes of this disclosure, "oral tolerance" or "oral tolerization" will include tolerance and tolerization via inhalation. Although not wishing to be limited by theory, it is believed that similar mechanisms are involved in both oral tolerization via feeding and tolerization via inhalation. Of course, immune tissues particular to the breathing passages and lungs are involved in tolerization by inhalation, as distinguished from the Peyer's patches involved in oral tolerization.

As used herein, the term "cerebrovascular disease" relates to an abrupt onset of a focal neurologic deficit which may remain constant, or it may rapidly improve, or it may progessively worsen. This abrupt onset of a nonconvulsive and focal neurologic deficit is referred to as a stroke or cerebrovascular accident, and generally encompasses cerbral ischemia, cerebral infarction, and cerebral hemorrhage.

As used herein, the term "ischemia" or "ischemic" relates to a medical event which is pathological in origin, or to a surgical intervention which is experimentally imposed on an animal model, wherein circulation to a region of a tissue or organ is impeded or blocked. The affected region is deprived of oxygen and nutrients as a consequence of the ischemic event. This deprivation leads to the injuries of infarction in the region affected. An extensive list of causes of ischemic stroke is provided in Table 1.

As used herein, the term "infarct" or "infarction" relates to a region of a tissue or organ subjected to ischemia and suffering the physiological sequelae of ischemia. Infarction results if the flow of blood is interrupted for more than several seconds. In addition to the causes and risk factors that may result in cerebral ischemia that are provided above, additional causes include dissection of the cervicocerebral arteries, especially that which results from trauma, and fibromuscular dysplasia. Infarction also relates to a region injured as a result of exposure to a hemorrhage. A list of causes of intracranial hemorrhage is provided in Table 2.

As used herein, the term "myelin" relates to a substance prevalent in the central nervous system and in nerve fibers emanating therefrom which surrounds or sheaths the axons of neurons (i.e., the myelin sheath). Myelin includes the components myelin basic protein (MBP) and proteolipid protein (PLP) which become autoantigens in various pathological conditions, including cerebral infarction under consideration in the present invention. When myelin or a component of myelin is used in oral tolerization according to the method of the invention, these substances may be derived from bovine or other nonhuman mammalian origins. They may also be recombinant human or nonhuman myelin component proteins, and they may be chemically synthesized myelin component proteins.

TABLE 1

Causes of Ischemic Stroke

Thrombosis

Atherosclerosis

Vasculitis

Collagen vascular disease: temporal (giant cell) arteritis, polyarteritis nodosa,
Wegener's granulatosis, Takayasu's arteritis, syphilis
Meningitis: tuberculosis, fungi, syphilis, bacteria, herpes zoster
Arterial dissection: carotid, vertebral, intracranial arteries at the base of the brain
Hematologic disorders: polycythemia, thrombocytosis, thrombotic thrombocytopenic
purpura, disseminated intravascular coagulation, dysproteinemias, hemogiobinopathies
(sickle cell disease)
Miscell aneous: cocaine, amphetamines, moyamoya diease, fibromuscular dysplasia,
Binswanger's disease
Embolism Cardiac sources: dysrhythmia, coronary heart disease, rheumatic heart disease, etc.
Atherothrombotic arterial sources: bifurcation of common carotid artery, carotid siphon,
distal vertebral artery, aortic arch
Unknown sources: may be associated with a hypercoagulable state secondary to
systemic disease, carcinoma (especially pancreatic), eclampsia, oral contraceptives,
lupus, factor C or S deficiency, factor V mutation, etc.
Vasoconstriction Vasospasm: cerbral vasospasm following subarchnoid hemorrhage
Reversible cerebral vasoconstriction: idiopathic, migraine, eclampsia, trauma
Venous Dehydration, pericranial infection, postpartum and postoperative states, systemic cancer

TABLE 2

Causes of Intracranial Hemorrhage

Spontaneous intracerebral hemorrhage: hypertensive, amyloid angiopathy
Ruptured aneurysm: saccular, mycotic
Ruptured arteriovenous malformation
Cocaine, amphetamines
Trauma
Bleeding with brain tumors
Systemic bleeding disorders, including anticoagulation therapy
Hemorrhagic infarction As used herein the term "effective" when describing a dose size, frequency, or duration, or the concept of dose "effectiveness," relates to a dosing which results in a reduction in the size and severity of an actual cerebral infarct, or to a probability that any such cerebral infarct, were it to occur, would be of reduced size and severity.

The present invention provides a new treatment for cerebral infarcts due to ischemic events as well as to hemorrhagic events. The method of treatment relates to minimizing the extent and severity of injury in the brain due to stroke by abrogating or minimizing inflammatory responses to the injury that would otherwise occur. The method involves induction of tolerance to potential autoantigens in the region affected by the stroke by means of administration, either orally or by inhalation, of such an antigen. In the present invention, the antigen administered is myelin or a component of myelin such as myelin basic protein or proteolipid protein. In the case where a patient has been diagnosed as having suffered a stroke, the administration of myelin should begin as soon as possible after the infarct occurred, preferably within a few days, or more preferably within a few hours, of the event. In the case where a patient is at risk of developing an infarct as a result of impending surgical or similar intervention or is otherwise at high risk of infarction, administration of myelin preferably begins as soon as the decision planning the intervention is made or the risk identified. In either case, the duration of the treatment is a few days, several days, or a few weeks, circumscribed by the time frame in which ischemic injury and acute inflammatory response to the resulting infarct is understood, or expected, to occur.

This method of treatment is distinguished from current practice in the field of immunology and in the treatment of stroke. Oral tolerization as a therapy for chronic conditions related to autoimmune diseases is currently contemplated in the field, and involves administration of the autoantigen for extended periods lasting several months or up to a year, or longer. Stroke is an acute rather than a chronic condition. Current treatments for stroke practiced in the field do not involve oral tolerization. Rather, they include procedures such as depleting the circulating pool of leukocytes (Dutka et al., Stroke 20: 390–395 (1989); Bednar et al., Stroke 22: 44–50 (1991)), inhibiting leucocyte function (Clark et al., Stroke 25: 1411–1415 (1994)), blocking leukocyte adhesion (Chopp et al., Stroke 25: 869–875 (1994); Mori et al., Stroke 23: 712–718 (1992)) and by administration of immunosuppressive drugs such as, for example, steroids, cyclosporin, and FK506.

In order to practice the method of the invention, the target group of subjects is to be identified. This group is composed of mammalian subjects at risk of developing a cerebral infarct. For human subjects, a victim of cerebral ischemia, or stroke, has an acute risk of developing a cerebral infarct as a consequence. Hemorrhagic stroke and trauma that produces contusion, for example, may also give rise to inflammatory responses such as edema. Infections such as herpes simplex encephalitis and cytomegalovirus infection additionally can result in immune-mediated injury. Stroke is identified by symptomology and diagnostic screening well known to physicians skilled in neurology and in circulatory disease. A human subject may also be a patient scheduled for imminent surgery or an invasive procedure that carries a high risk of inducing cerebral ischemia as an undesired result of carrying out the procedure. Such procedures include, but are not limited to, heart bypass, angioplasty, and the like. Further, a human subject at risk for developing cerebral ischemia by genetic predisposition to stroke or by having a medical condition that is understood to increase the probability of incurring cerebral infarct may also be treated by the method of this invention. Such medical conditions include, by way of nonlimiting examples, atherosclerosis, previous stroke or transient ischemic attacks, diabetes mellitus, hypertension, hypercholesterolemia, and a history of smoking. A comprehensive list of causes of cerebral ischemia is provided in Table 1. A list of causes of cerebral hemorrhage is provided in Table 2.

A nonhuman mammal is identified as a subject if the animal is to be subjected to procedures that induce cerebral ischemia and lead to cerebral infarction, or is to undergo surgical or invasive procedures comparable to those identified in the preceding paragraph for human subjects.

In the practice of the invention, oral tolerization as defined above is undertaken by administering to the subject an immunotolerizing dose of the autoantigen myelin or a component thereof such as MBP or PLP. The myelin component administered may also be a peptide fragment of myelin basic protein. Wang et al. (1992) have shown that patients who have suffered ischemic cerebrovascular damage have T cells reactive to peptides such as MBP peptides 110–128 or MBP 148–165; it is possible that peptides derived from myelin components may have tolerizing properties as well. In the case of a victim of stroke, a dose may be administered by one of several techniques such as voluntary ingestion, intubation into the stomach of the required dose, inhalation of an aerosol containing the autoantigen, and the like. In the case of a human that is not a stroke victim, the dose may be administered by procedures such as voluntary ingestion, inhalation, or the like. In the case of a nonhuman mammal, the dose may be administered by procedures such as, for example, gavage, gastric intubation, other oral means known to those of skill in the handling of nonhuman mammals, or inhalation of an aerosol, and the like.

Myelin to be administered in the method of the invention encompasses the components myelin basic protein and proteolipid protein. The myelin or a component of myelin is obtained from bovine or other nonhuman mammalian origins. The myelin components may also be recombinant human or nonhuman myelin component proteins. They may also be chemically synthesized myelin component proteins. The myelin component may furthermore be a fragment of myelin basic protein or of proteolipid protein.

Voluntary ingestion of the autoantigen bovine myelin has been described by Weiner et al. (Science 259: 1321–1324 (1993)). Various oral dosage forms are well known to those of skill in the fields of pharmaceutical sciences. Examples of oral dosage forms have been summarized in U.S. Pat. No. 5,643,868, which is incorporated herein by reference. These include pharmaceutical formulations intended for ingestion containing, in addition to the autoantigen, pharmaceutically acceptable carriers, diluents, solubilizers, emulsifiers, and the like. Additionally the autoantigen may be incorporated into tablet, capsule, or lozenge dosage forms, or may be further incorporated into dosage forms that minimize digestion in the stomach if so desired.

Aerosol delivery systems are also well known to practitioners in the pharmaceutical sciences. Aerosol preparations are disclosed in U.S. Pat. Nos. 5,643,868, 5,645,820, 5,641,474, and 5,571,500 which are incorporated herein by reference.

The size of the dose of myelin or a component such as MBP or PLP to be administered depends on the route of administration and the medical condition of the subject. The bioavailability of an autoantigen in oral dosage forms will, of course, depend on the particular characteristics of the dosage form chosen. The bioavailability of an autoantigen in an aerosol administered by inhalation is expected to differ from that generally obtained upon oral administration. Administration of the autoantigen to a stroke victim represents the most acute situation of those considered in this invention, since the ischemic event has already occurred and the need for immediate minimization of injury from infarction is extreme. This may necessitate a particular size of dose appropriate for the circumstances. A human subject or nonhuman animal scheduled for imminent surgery or medical intervention is in a somewhat less acute medical state. As a result the size of each dose may be different, and may be open to somewhat greater variation and still be within the practice of the invention. In general, the size of each dose for oral administration may range from about 0.2 g to about 10 g for a human adult (or from about 4 mg/kg body weight to about 100 mg/kg body weight), and for administration by inhalation administration may range from about 0.2 g to about 10 g for a human adult. Dose sizes for nonhuman mammals generally fall in the same range on a g/kg basis.

For the reasons just summarized, the frequency of dosing may also vary. A more acute medical status may suggest a different dosing regime than one that is somewhat less acute. In general, the invention may be practiced by administering doses at a frequency ranging from about once or twice per week to about once daily. Preferably, the dosage is from about 0.2 g to about 10 g per day for a period of at least 3 days.

Likewise for the reasons given above, the duration of dosing is subject to variability. A stroke victim, being in an extremely acute medical condition, requires the effect of the method of the invention to be realized as early as possible. This clearly dictates a course of dosing that emphasizes a short duration. A subject facing scheduled surgery or medical intervention, or being otherwise at high risk for a stroke, having a less acute medical status, may be subjected to dosing for a different, generally longer, duration. In general, a victim of stroke may be administered the oral antigen for a duration ranging from about 3 days to about 10 days. On the other hand, a subject who is about to undergo medical or surgical treatment which enhances the risk of ischemia in the brain may undergo dosing for a duration ranging from about 5 days to about 14 days. A subject who is at risk for developing a cerebral infarct associated with a chronic medical condition such as a genetic predisposition to stroke, diabetes mellitus, hypertension, hypercholesterolemia, and a history of smoking can be treated for a duration of at least 5 days.

Dosage regimes can also start at low dosages in order to assess tolerance, and then build up to higher levels. It is also envisioned that "boosters" of low dosages could be administered at periodic intervals.

The method of the present invention is effective to minimize the size and severity of an infarct in the brain of the subject. The size of an infarct in a human patient having suffered a stroke may be determined, for example, by various noninvasive radiological procedures known to those of skill in the field of medicine, especially to those of skill in radiology and neurology. Examples of methods available in the field include, but are not limited to, magnetic resonance imaging, ultrasonic imaging, and targeted radiotracer imaging. The size of an infarct in a nonhuman mammal having been subjected to procedures which have produced a cerebral infarct, may be determined by similar noninvasive procedures as those available for use with human patients. In addition, in cases where a nonhuman mammal dies in the course of an experiment, the size of the infarct may be established by direct observation, by post mortem anatomical and histological examination. Such procedures are well known to those of skill in the fields of veterinary medicine, pathology, physiology, anatomy, and related fields.

The severity of an infarct in a human patient having suffered a stroke may be determined, for example, by various symptomatic and diagnostic procedures known to those of skill in the fields of medicine, especially to those of skill in neurology, hematology, and physical medicine, in addition to assessing the results of radiological and anatomical diagnosis that were discussed in the preceding paragraph. Kinetic, sensory, and cognitive behavior is affected in stroke patients. Medical diagnosis routinely includes such assessments in analysis of the status of stroke victims. In addition, stroke patients may be diagnosed by the methods of hematology. These may be used to assess the populations and cellular characteristics of immune cells in the circulation, as well as various enzymatic activities or cellular components from brain tissue. These activities or components are generally found in the blood of stroke victims but are typically absent or present at only low levels in subjects that have not suffered a stroke. Similar procedures may be applied to nonhuman mammals who have suffered ischemic injury as a result of medical or surgical procedures. The amounts or values of the various results obtained in these diagnostic tests may be evaluated with respect to values known in the various fields to represent normal or pathological states. As a result of evaluating the group of diagnostic results obtained as outlined above, the severity of the infarction may be assessed by workers of skill in the medical fields. The dose size, frequency, and the duration of treatment by the method of the present invention may be adjusted accordingly based on the severity of the infarction and the general medical condition of the patient.

The following example is intended more fully to describe the invention. It is not intended to limit the scope of the invention in any way.

EXAMPLE
Experimental Cerebral Infarction in Rats

Method of Statistical Analysis

Data are expressed as mean ± (standard error of the mean). Statistical significance was determined by repeated measures ANOVA (infarct size) or by one-way ANOVA with post hoc Dunnett's test (immune responses). All tests were two-tailed and significance was set at $p<0.05$.

Induction of Cerebral Infarct

Male Lewis rats (6–10 weeks old) were tolerized to bovine MBP (Sigma Chemical Co., St. Louis, Mo.) (OT-MBP, n=23) by repetitive gavage with 1 mg of protein in 0.5 ml phosphate buffered saline (PBS) every 2–3 days for 2 weeks, for a total of 5 feedings. A second group of animals was fed ovalbumin (OVA) (Sigma Chemical Co., St. Louis, Mo.) (1 mg/0.5 ml PBS) on a similar schedule (CONTROL, n=38). A third group of animals was sensitized to MBP (SENS-MBP, n=6) by injection of guinea pig MBP (a gift from Laura Quigley, National Institute of Neurological Disease and Stroke) (50 $\mu$g MBP/50 $\mu$l PBS mixed with an equal amount of complete Freund's adjuvant (CFA; Sigma Chemical Co., St. Louis, Mo.)).

Two days after the last feeding (OT-MBP and CONTROL) or 6 days after immunization (SENS-MBP) the middle cerebral artery was occluded (MCAO) under halothane anesthesia (2%) via a 4.0 monofilament suture inserted into the internal carotid artery and advanced approximately 17–20 mm (Zea-Longa et al., Stroke 20: 84–91 (1989)). In sham-operated animals, the suture was inserted into the carotid artery but not advanced (OT-MBP, n=11; CONTROL, n=9). The average duration of surgery and anesthetic administration was 15 minutes. Body temperature was continuously monitored during surgery and maintained at 37–38° C. with a thermostatically controlled warming blanket; animals were allowed to thermoregulate thereafter. Three hours after MCAO, reperfusion was established by withdrawing the suture under brief anesthesia. Sham-operated animals underwent the same brief period of anesthesia. Animals were sacrificed by cardiac puncture and decapitation under halothane anesthesia.

Infarct Size

In the first experiment, animals were sacrificed 24 hours after ischemia, i.e., after 21 hours of reperfusion (OT-MBP, CONTROL). Brains were sectioned coronally and incubated in 2% triphenyl tetrazolium chloride (TTC) at 38° C. for 30 minutes. Infarct size was determined using a digitized imaging system (NIH Image). Sections stained with TTC were analyzed at 5 predetermined levels (bregma +1.00, −0.40, −1.80, −3.20, and −4.40, corresponding to coronal levels 1, 2, 3, 4, and 5 respectively, in FIG. 1). Both direct and indirect measurements (which correct for the presence of edema (Swanson et al., J. Cereb. Blood Flow Metab. 10: 290–293 (1990))) were made.

Figure 1:
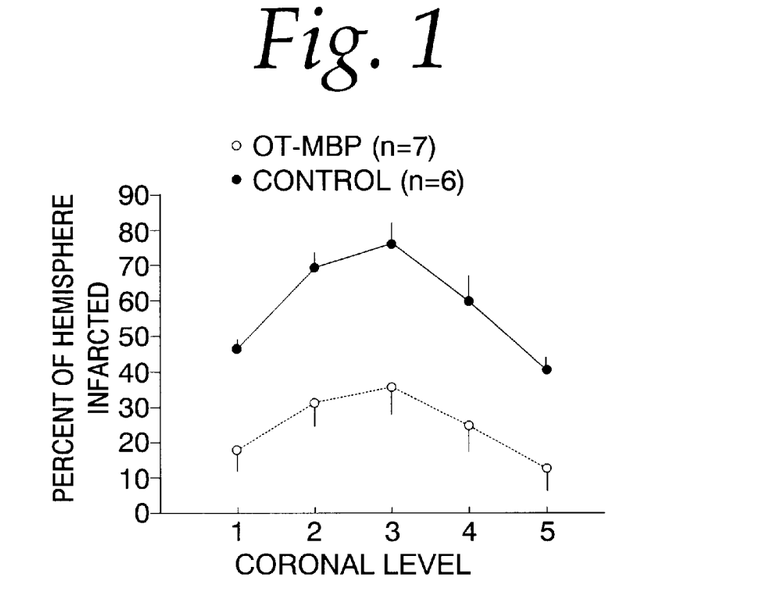
FIG. 1. This figure illustrates infarct size at 5 predetermined coronal levels 24 hrs after ischemia in animals orally treated with MBP (TO-MBP; n=7) and CONTROL (n=6) animals as detected by TTC staining.

In this experiment there was a non-significant trend towards decreased mortality in OT-MBP animals (12.5%, n=8) as compared to CONTROL animals (46.7%, n=15). Infarct size 24 hours after ischemia was significantly less in OT-MBP as compared to CONTROL animals at each of the 5 levels assessed (FIG. 1). Groups differ from each other as determined by repeated measures ANOVA (p<0.05). Infarcts had the features of pan-necrosis.

Figure 2:
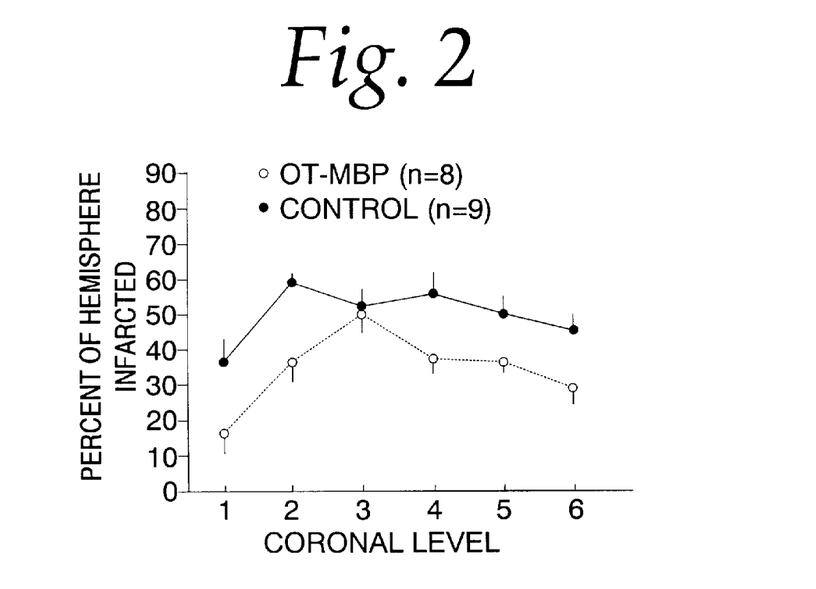
FIG. 2. This figure illustrates infarct size 4 days after middle cerebral artery occlusion (MCAO), measured on cresyl violet stained sections.

In the second experiment, animals were sacrificed 4 days after ischemia, brains frozen, sectioned coronally at 16 μm intervals (marked necrotic injury prevented thinner sectioning), and stained with cresyl violet. Sections were analyzed at 6 predetermined levels (bregma +2.40, +1.00, −0.40, −1.80, −3.20, and −4.40, corresponding to coronal levels 1, 2, 3, 4, 5, and 6, respectively, in FIG. 2). Both direct and indirect measurements were made.

In this experiment, there was a trend towards decreased mortality at 4 days in OT-MBP animals (33.3%, n=15) as compared to CONTROL animals (56.5%, n=23). There was a 100% 4 day mortality among the SENS-MBP group (n=6). Limited necropsy revealed herniation as the etiology of death. The differences in 4-day mortality among OT-MBP, CONTROL and SENS-MBP animals were not statistically significant.

Infarct size 4 days after ischemia, corrected for the presence of edema, was significantly less in OT-MBP animals (n=8) than in CONTROL animals (n=9) (FIG. 2), as also found at 24 hours. Groups differ from each other as determined by repeated measures ANOVA (p<0.05).

Delayed Type Hypersensitivity (DTH)

Animals were tolerized to MBP (n=4) or ovalbumin (OVA, n=3). CONTROL animals (n=4) were not handled. All animals were then immunized with bovine MBP (50 μg MBP in 50 μl PBS mixed with 50 μl CFA) injected into the hind footpad, and then rechallenged with bovine MBP (50 μg MBP in 50 μl PBS) injected into the ear 15 days later. Change in ear thickness was measured with microcalipers (Mitutoyo, Japan) 48 hours later by an observer blinded to treatment.

Animals fed MBP prior to immunization with bovine MBP had a significant decrease in DTH response, as determined by increase in ear thickness (0.059 mm±0.039; p<0.05), compared to animals fed OVA (0.228 mm±0.044) or control animals (0.180 mm±0.032). This result confirms the efficacy of the tolerizing regimen and indicates that the tolerance is antigen-specific.

Systemic Immune Response

As a measure of systemic immunological response, the total number of spleen cells was determined. The spleens were removed, and single cell suspensions prepared in RPMI-1640 media (supplemented with 10% fetal calf serum, 2-mercaptoethanol, sodium pyruvate, non-essential amino acids, L-glutamine, penicillin-streptomycin, and HEPES) and cultured in microtiter well plates at $1.5 \times 10^4$ cells/well in 0.2 ml/well. Cell culture reagents were purchased from GIBCO Life Technologies, Grand Island, N.Y. Cells were cultured with the T-cell mitogen concanavalin A (4 μg/ml), the B-cell mitogen lipopolysaccharide (LPS; E. Coli, serotype 0111: B4; 0.25 μg/ml), or bovine MBP (25 μg/ml) for 144 hours. The mitogens were obtained from Sigma Chemical Co., St. Louis, Mo. Proliferation was assessed by pulsing cells with 1 μCi/well [methyl-$^3$H] thymidine (specific activity 25 Ci/mmol; Amersham Corp., Arlington Heights, Ill.) for the final 18 hours of culture and harvesting onto glass fiber filters (Skatron, Sterling Va.) using a multi-channel harvesting device (Mash II, Skatron, Sterling, Va.). Incorporation of [methyl-$^3$H] thymidine was measured by liquid scintillation spectroscopy and results expressed as stimulation indices (SI). The SI is calculated by dividing the counts per minute of the mitogen- or antigen-stimulated cells by the counts per minute of cells incubated in media alone. All cultures were performed in quadruplicate.

There were no significant differences in SI among the experimental groups at either 24 or 96 hours for concanavalin A stimulation (OT-MBP=64.4±13.0 and 54.8±11.1; CONTROL=53.1±8.06 and 79.5±14.0, respectively). Naive animals had SI=90.2±15.4 to concanavalin A stimulation. Similarly, there were no significant differences in proliferation to LPS at 24 (OT-MBP=1.53±0.84, CONTROL= 1.89±0.45) or 96 hours (OT-MBP=7.86±2.32, CONTROL= 7.02±2.61). These results, indicating no differences in mitogen-induced splenocyte proliferation among experimental and control animals, suggests that the neuroprotection conferred by oral tolerance is not due to generalized immunosuppression.

Cells from sham-operated OT-MBP animals evidenced a significant increase in proliferation to MBP (3.00±1.29; p<0.05) 96 hours after surgery, compared to naive animals (1.00±0.13). This proliferation was suppressed with ischemia (1.40±0.15). MBP induced splenocyte proliferation in ischemic CONTROL (1.93±0.72) and sham-operated CONTROL (1.27±0.29) animals was no greater than in naive animals. The pattern of increased MBP responsiveness that is suppressed by ischemia has been documented previously (Husby et al., J. Immunol. 152: 4663–4670 (1994)) and suggests that there is antigen-specific priming of T-cells due to oral tolerization that requires antigen re-exposure to induce the immunosuppressive phenotype.

We claim:

1. A method of treating a mammalian subject at risk of developing a cerebral infarct, the method comprising administering a central nervous system myelin or a central nervous system myelin component to the subject either orally or by inhalation in an amount and for a duration of time effective to minimize the size and severity of a cerebral infarct that may occur in the subject.

2. The method described in claim 1, wherein the risk of developing the cerebral infarct is associated with an acute medical condition, impending acute medical or surgical treatment, or a chronic medical condition.

3. The method described in claim 2, wherein the subject is a human and the risk is associated with an acute medical condition which is selected from the group consisting of an ischemic or hemorrhagic stroke, trauma, herpes simplex encephalitis, and cytomegalovirus infection.

4. The method described in claim 3, wherein the duration of administering myelin or a myelin component ranges from about 3 days to about 10 days.

5. The method described in claim 2, wherein the subject is a human and the risk is associated with impending medical or surgical treatment which enhances the risk of ischemia in the cerebrum.

6. The method described in claim 5, wherein the duration of administering myelin or a myelin component ranges from about 5 days to about 14 days.

7. The method described in claim 2, wherein the subject is a human and the risk is associated with a chronic medical condition selected from the group consisting of a genetic predisposition to stroke, atherosclerosis, previous stroke or transient ischemic attacks, diabetes mellitus, hypertension, hypercholesterolemia, and a history of smoking.

8. The method described in claim 7, wherein the duration of administering myelin or a myelin component is at least 5 days.

9. The method described in claim 2, wherein the subject is a nonhuman mammal and the risk is associated with impending acute medical or surgical treatment, the mammal being one on which experimental procedures that incur the risk of producing cerebral ischemia are to be, or are being, performed.

10. The method described in claim 9, wherein the duration of administering myelin or a myelin component ranges from about 5 days to about 14 days.

11. The method described in claim 1, wherein myelin is administered.

12. The method described in claim 1, wherein a myelin component is administered.

13. The method described in claim 1, wherein the route of administration is oral.

14. The method described in claim 13, wherein the dose of myelin or a myelin component administered ranges from about 4 mg/kg body weight to about 100 mg/kg body weight, the dose being administered at a frequency of about once every 7 days to about once every day.

15. The method described in claim 1, wherein the route of administration is by inhalation.

16. The method described in claim 15, wherein the dose of myelin or a myelin component administered ranges from about 4 mg/kg body weight to about 100 mg/kg body weight, the dose being administered at a frequency of about once every 7 days to about once every day.

17. A method of treating a mammalian subject at risk of developing cerebrovascular disease, the method comprising administering a central nervous system myelin or a central nervous system myelin component to the subject either orally or by inhalation in an amount and for a duration of time effective to minimize the size and severity of a cerebral infarct that may occur in the subject.

18. A method of treating a mammalian subject at risk of developing a cerebral infarct, the method comprising administering a central nervous system myelin component chosen from the group consisting of myelin basic protein, proteolipid protein, a peptide fragment of myelin basic protein, and mixtures thereof to the subject either orally or by inhalation in an amount and for a duration of time effective to minimize the size and severity of a cerebral infarct that may occur in the subject.

19. The method described in claim 18, wherein the myelin component is myelin basic protein.

20. The method described in claim 18, wherein the myelin component is proteolipid protein.

21. The method described in claim 18, wherein the myelin component is a peptide fragment of myelin basic protein.

* * * * *